United States Patent [19]

Shiio et al.

[11] Patent Number: 4,601,982

[45] Date of Patent: Jul. 22, 1986

[54] **METHOD FOR PRODUCING L-TRYPTOPHAN BY FERMENTATION WITH A *BREVIBACTERIUM FLAVUM* MUTANT**

[75] Inventors: Isamu Shiio, Kamakura; Shinichi Sugimoto; Kazue Kawamura, both of Kawasaki, all of Japan

[73] Assignee: Ajinomoto Company Incorporated, Tokyo, Japan

[21] Appl. No.: 367,334

[22] Filed: Apr. 12, 1982

[30] Foreign Application Priority Data

Apr. 20, 1981 [JP] Japan .................................. 56-59570

[51] Int. Cl.$^4$ ...................... C12P 13/22; C12N 15/00; C12R 1/13
[52] U.S. Cl. .................................... 435/108; 435/840; 435/172.1
[58] Field of Search ................ 435/108, 253, 172, 840

[56] References Cited

U.S. PATENT DOCUMENTS 3,700,559 10/1972 Shiio et al. .......................... 435/108
4,560,652 12/1985 Kurahashi et al. ................. 435/108

*Primary Examiner*—Thomas G. Wiseman
*Assistant Examiner*—Elizabeth C. Weimar
*Attorney, Agent, or Firm*—Oblon, Fisher, Spivak, McClelland & Maier

[57] ABSTRACT

A method for producing L-tryptophan by fermentation, which comprises, culturing aerobically in a culture medium a mutant of the genus Brevibacterium which is resistant to azaserine and tryptophan analogue and capable of producing L-tryptophan, and recovering the L-tryptophan which accumulates in the culture medium.

1 Claim, No Drawings

METHOD FOR PRODUCING L-TRYPTOPHAN BY FERMENTATION WITH A *BREVIBACTERIUM FLAVUM* MUTANT

BACKGROUND OF THE INVENTION

The present invention relates to a method for producing L-tryptophan by fermentation.

L-tryptophan, which is one of the essential amino acids and an essential component in human and animal nutrition, is known to be synthesized by a variety of routes such as starting with β-indolylaldehyde and hippuric acid (Ber. 39, 2515, 1906) or starting with α-ketoglutaric acid and phenyl hydrazone (U.S. Pat. No. 3,019,232). Other than these chemical synthetic process, it is known that L-tryptophan is produced from its precusors such as an antranilic acid, indole or 3-indole pyruvate by an action of microorganisms.

It is also known that L-tryptophan is produced by a fermentation process in which L-tryptophan producing mutants of the genus Brevibacterium are used. And various L-tryptophan producing mutants, produced by the artificial mutation of wild strains of microorganisms of the genera Brevibacterium or Corynebacterium, are known. Examples of such artificial mutants are mutants resistant to tryptophan analogue such as 5-methyl tryptophan (Japanese Published Examined patent application No. 18828/1973), mutants resistant to tryptophan analogue and phenylalanine analogue, and mutants resistent to these analogue and further requiring L-amino acid such as L-tyrosine, L-phenylalanine, L-methionine L-histidine for their growth (Japanese Published Unexamined patent application Nos. 42091/1975, 129791/1975, Japanese Published Examined patent application No. 19037/1976 and Agr, Biol, Chem., 39, 343(1975)).

Recently, there is a great demand for L-tryptophan as a feed stuff but the demand can not be supplied because L-tryptophan can not be produced at a reasonable price by any fermentation process or chemical synthetic process even though various process for producing L-tryptophan are known as stated above.

SUMMARY OF THE INVENTION

Accordingly, one object of the present invention is to provide a method for preparing L-tryptophan in improved yield by a fermentation process.

Briefly, this object and other objects of the present invention as hereinafter will become more readily apparent can be attained in a method for producing L-tryptophan by fermentation by aerobically culturing a mutant of the genus Brevibacterium which is resistant to azaserine and tryptophan analogue and recovering L-tryptophan accumulated in a culture medium.

DETAILED DESCRIPTION OF THE PREFERRED EMBODIMENTS

It has now been found that the production of L-tryptophan can be increased when resistance to azaserine is imparted to a known tryptophan analogue resistant and L-tryptophan producing mutant of the genus Brevibacterium.

The microorganisms employed in the present invention are mutants which belong to the genus Brevibacterium and are resistant to azaserine and tryptophan analogue and capable of producing L-tryptophan in a greater yield.

Azaserine (serine diazoacetate; O-diazoacetyl-L-serine) is one of the antibiotics produced by microorganisms of the genus Streptomyces having an antineoplastic activity and is known as one of the glutamine antagonists.

Tryptophan analogue of the present invention are such chemicals as those which inhibit the growth of the microorganims of the genus Brevibacterium and the inhibition is suppressed when L-tryptophan coexists in the medium. And tryptophan analogue includes lower alkyltryptophan such as 5-methyl tryptophan and 6-methyltryptophan, halogenotryptophan such as 5-fluorotryptophan and 6-fluorotryptophan, tryptophan hydroxamate and 7-azatryptophan.

According to a preferred embodiment of the present invention, a known characteristics useful for the production of L-tryptophan such as requirement of L-phenylalanine, L-tyrosine or L-methionine, and resistance to phenylalanine analogue is imparted to the mutants of the present invention although mutant having such a characteristics as stated above only does not produce L-tryptophan.

The representative mutant specimen of the present invention is;

*Brevibacterium flavum* AJ 11667 FERM-P 5907 FERM BP-114 (5-FT$^r$, p-F-Phe$^r$, AS$^r$, Tyr$^-$, Met$^-$)

wherein the abbreviation in parenthesis have the following meanings;

5-FT$^r$: resistance to 5-fluorotryptophan
AS$^r$, p-F-Phe$^r$: resistance to azaserine, p-fluorophenylalanine
Tyr$^-$, Met$^-$: requirement of L-tyrosine, L-methionine for their growth The mutant identified above by FERM BP number was originally deposited with the FERM-P number on Mar. 10, 1981 at the Fermentation Research Institute, Agency of Industrial Sciences and Technology, Ministry of International Trade and Industry (FRI), 1-3, Higashi 1-Chome, Yatabe-machi, Tsukuba-gun, Ibaragi-ken 305, Japan and the deposit was converted to deposit under the Budapest Treaty on Mar. 29, 1982 with FRI which has aquired the status of an International Depository Authority as of May 1, 1981. The mutants of the present invention as mentioned above can be induced from parent microorganism strains by any conventional mutation method.

The first step of the induction is to mutate the parent strains with a suitable chemical mutagen such as N-methyl-N'-nitro-n-nitrosoguanidine and nitrous acid or with irradiation by ultraviolet light. The second step of the process is to select resistant mutants by picking up colonies of the microorganisms grown on plates of a nutrient agar medium containing an amount of azaserine which inhibits the growth of the parent strains. Thereafter, the mutants are evaluated for L-tryptophan productivity by a standard method.

Suitable parent strains from which the present mutants can be induced include mutants which are resistant to tryptophan analogue and capable of producing L-tryptophan, or wild strains, of the genus Brevibacterium.

The preferred mutants resistant to tryptophan and analogue are, for example:

*Brevibacterium flavum* AJ 3246 ATCC 21427 (5-MT$^r$, Phe$^-$, Tyr$^-$)
*Brevibacterium flavum* AJ 11353 FERM-P 5006 (5-FT$^r$, p-F-Phe$^r$, Met$^-$, Tyr$^-$)

5-MT$^r$: resistant to 5-methyltryptophan

When wild strains are used as the parent strains, resistance to tryptophan is imparted to the wild strains prior to or after imparting resistance to azaserine to the wild strains.

The preferred wild stains of the genus Brevibacterium are coryne-form L-glutamic acid producing bacteria and the examples include:

Brevibacterium flavum ATCC 14067
Brevibacterium lactofermentum ATCC 13869
Brevibacterium saccharolyticum ATCC 14066
Brevibacterium divaricatum ATCC 14020

The degree of resistance to azaserine of the mutant AJ 11667 derived from Brevibacterium flavum AJ 11668 is shown in the following Experiment.

Experiment

Agar plates (8.5 cm in diameter) of the minimum medium of which the composition is given in Table 1 further containing 200 microgram/ml azaserine or 500 microgram/ml 5-fluoro-DL-tryptophan were prepared.

TABLE 1

| Composition of Minimum Medium | |
|---|---|
| Component | Amount per 1.0 liter |
| Glucose | 20 g |
| Ammonium sulfate | 10 " |
| Urea | 3 " |
| KH$_2$PO$_4$ | 1 " |
| MgSO$_4$.7H$_2$O | 0.4 " |
| FeSO$_4$.7H$_2$O | 10 mg |
| MnSO$_4$.4H$_2$O | 8 " |
| Sodium chloride | 0.5 g |
| d-Biotin | 50 microgram |
| Thiamine.HCl | 200 " |
| L-Methionine | 150 mg |
| L-Tyrosine | 100 " |
| Agar | 20 g |

Each strain grown on an agar slant of the minimum medium was inoculated on the plate; the inoculum size being adjusted to 10$^6$ cells per plate. Then the plate was incubated at 30° C. for 4 days and numbers of the colonies of the microorganisms grown on the plate were counted. The results obtained are shown in Table 2.

TABLE 2

| | Degree of resistance | | |
|---|---|---|---|
| | number of colonies per plate | | |
| Chemical | AJ 11667 | AJ 11353 | AJ 11668 |
| None | ++ | ++ | ++ |
| 5-fluorotryptophan | ++ | ++ | − |
| azaserine | ++ | − | − |

++: number of colonies is more than 1000
−: colony was not formed

AJ 11668 in Table 2 is the parent strain of AJ 11667 and is resistant to p-fluorophenylalanine.

The mutants of the present invention are cultured aerobically in a culture medium containing carbon sources, nitrogen sources, and inorganic ions, and when required, minor nutrients.

Suitable carbon sources include saccharides such as glucose, fructose and sucrose, and molasses and hydrolyzed starch containing these saccharides; organic acid such as acetic acid and citric acid; and alcohols.

Suitable nitrogen sources include, for example, ammonium sulfate, ammonium nitrate, gaseous ammonia and urea. As the inorganic ions, K$^+$, Na$^+$, Ca$^{++}$, Fe$^{++}$, Mn$^{++}$, Mg$^{++}$, Zn$^{++}$, SO$_4^{--}$, Cl$^-$ and PO$_4^{---}$ ions are suitably added to the culture medium when required.

Suitable minor nutrients include amino acids, vitamin yeast extract, peptone, and hydrolyzed soy protein.

With mutants requiring nutrient elements such as L-amino acids, the nutrient elements are added to the culture medium.

Cultivation is carried out preferably under aerobic condition, for 1 to 4 days at a temperature ranging from 20° to 40° C. with preferable adjustment of the pH of the culture medium to 5.0 to 9.0 with an organic or inorganic acid or alkali. For this purpose, urea, CaCO$_3$, and gaseous ammonia are preferably used.

The L-tryptophan accumulated in the culture medium may be recovered by an entirely conventional recovering technique such as those which use an anion-exchanging resin.

Having generally described this invention, a further understanding can be obtained by referance to certain specific example which is provided herein for purpose of illustration only and is not intended to be limiting unless otherwise specified.

EXAMPLE

Twenty ml portions of the culture medium of which the composition is given in Table 3 were placed into 500 ml flasks which were then heated at 110° C. for 10 minutes. Thereafter, the contents of each flask were supplemented with 1.0 g CaCO$_3$ separately sterilized.

TABLE 3

| Composition of Culture Medium (pH 6.5) | |
|---|---|
| Component | Amount per 1.0 liter |
| Glucose | 130 g |
| Ammonium sulfate | 25 " |
| KH$_2$PO$_4$ | 1.0 " |
| Fumalic acid | 12 " |
| Acetic acid | 3 ml |
| MnSO$_4$.4H$_2$O | 8 mg |
| d-Biotin | 50 microgram |
| Thiamine HCl | 2.0 mg |
| L-Tyrosine | 650 " |
| DL-Methionine | 400 " |
| MgSO$_4$.7H$_2$O | 1.0 g |
| Soy protein hydrolyzed (TN 2.4%) | 50 ml |

Each strain for testing shown in Table 4 which has previously cultured on an agar slant of the same culture medium was inoculated into a batch of the culture medium, and cultured with shaking at 30° C. for 72 hours.

After the cultivation, the determination of the L-tryptophan which accumulated in the culture broth was conducted according to a standard bio-assay method using Leuconostoc mesenteroides ATCC 8042 and the results obtained as shown in Table 4.

TABLE 4

| Amount of L-Tryptophan accumulated | |
|---|---|
| Strain No. | L-Tryptophan (mg/ml) |
| AJ11668 (p-F—Phe$^r$) | 0.0 |
| AJ11353 (5FT$^r$,p-F—Phe$^r$,Met$^-$,Tyr$^-$) | 7.1 |
| AJ11667 (5FT$^r$,AS$^r$,p-F—Phe$^r$,Met$^-$,Tyr$^-$) | 9.1 |

A culture broth of AJ 11667 prepared in the same manner as described above was collected and centrifuged to remove microbial cells and CaCO$_3$.1.0 liter supernatant solution thus obtained was passed through a column of "Daiaion SK 104" in the acid form. By this procedure L-tryptophan was adsorbed on the resin, and it was eluted with 0.5N NH₄OH. The elute was evaporated and cooled to a temperature low enough to crystalize L-tryptophan.

Then crude crystalline L-tryptophan was dissolved into an aliquot of 50% ethanol solution and an active carbon was added to the solution. After decolorization was conducted, 5.4 g crystalline L-tryptophan was obtained from the decolorized solution.

What is claimed as new and desired to be secured by Letters Patent of the United States is:

1. A method for producing L-tryptophan by fermentation, which comprises:
culturing aerobically in a culture medium *Brevibacterium flavum* FERM BP 114, which is resistant to azaserine and tryptophan analogue and capable of producing L-tryptophan; and recovering the L-tryptophan which accumulates in the culture medium.

* * * * *